United States Patent [19]

Wright et al.

[11] 4,370,494

[45] Jan. 25, 1983

[54] CONVERTING ENZYME INHIBITORS

[75] Inventors: George C. Wright; Ronald E. White, both of Norwich, N.Y.

[73] Assignee: Norwich Eaton Pharmaceuticals, Inc., Norwich, N.Y.

[21] Appl. No.: 339,683

[22] Filed: Jan. 15, 1982

[51] Int. Cl.³ .......................................... C07C 101/26
[52] U.S. Cl. .................................................. 562/450
[58] Field of Search ........................ 560/41; 562/450; 424/319

[56] References Cited

U.S. PATENT DOCUMENTS 4,250,183  2/1981  Krastinat ............................. 562/450

Primary Examiner—James H. Reamer
Attorney, Agent, or Firm—Anthony J. Franze

[57] ABSTRACT

The compound N-(1-carboxy-3-phenylpropyl)glycyl-N'-(2,3-dihydro-1H-indene-1-yl)glycine is useful as an angiotensin I converting enzyme inhibitor.

1 Claim, No Drawings

CONVERTING ENZYME INHIBITORS

This invention is concerned with N-(1-carboxy-3-phenylpropyl)glycyl-N'-(2,3-dihydro-1H-indene-1-yl)glycine of the formula:

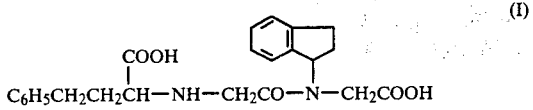

(I)

This compound is a potent inhibitor of the enzyme responsible for converting the decapeptide angiotensin I to the octapeptide angiotensin II. Angiotensin II is the powerful pressor agent implicated as the causative agent in some forms of hypertension.

Of late it has been recognized that a substance capable of interrupting the pathway whereby angiotensin II is produced, viz., the conversion hereabove referred to, presents a useful and effective means of combatting hypertension associated with that pressor agent.

It has been discovered that the compound of this invention is possessed of noteworthy activity in inhibiting angiotensin I converting enzyme. Thus, in in vitro techniques designed to evince such activity, this compound is highly effective. For example, it inhibits the pure converting enzyme isolated from rabbit lung tissue at a level of about 0.22 $\mu$m. It is, therefore, a notable angiotensin I converting enzyme inhibitor.

The compound of this invention is not limited to an in vitro manifestation of its converting enzyme inhibiting propensity. Upon oral administration, a dose-dependent antihypertensive effect in acute aortic coarctation hypertension rats is elicited. Oral dosage of about 10 mg/kg administered as a suspension in 0.5% Methocel solution achieves a reduction of about 12 mm Hg in mean arterial blood pressure in such rats.

The compound of this invention can be composed in a variety of dosage forms such as tablets, capsules, solutions and the like for convenient administration employing classical excipients and adjuvants with which there is no incompatibility. Such dosage forms contain from 10 to 500 mg of a compound of formula (I) in a unit dosage form in accordance with accepted pharmaceutical practice.

In order that this invention may be readily available to and understood by those skilled in the art, the following example represents a now preferred method for the preparation thereof.

A. N-(Indanyl)glycine Sodium Salt

Glycine (5.1 g, 0.068 mole) was dissolved in a solution of NaOH (2.72 g, 0.068 mole) and methanol (125 ml). To this was added 1-indanone (10.0 g, 0.076 mole, 10% excess) and 5% Pd/C dry (2.0 g). This mixture was subjected to hydrogen at room temperature on a Parr shaker for 24 hours. The catalyst was removed by filtration and fresh 5% Pd/C dry (2.0 g) added. Hydrogenation was resumed for 20 hours. A total of 55 psi of $H_2$ (68 psi theory) was taken up. The catalyst was removed by filtration and the filtrate concentrated under reduced pressure to an oily residue. This residue was dissolved in $H_2O$ (100 ml) and extracted with ethyl acetate (3×25 ml). The aqueous solution was cooled on an ice bath and a white solid precipitated. This solid was collected and air dried to give 5.0 g of crude product. A second crop was obtained by concentrating the filtrate under reduced pressure to a solid residue. This residue was recrystallized from 70% isopropanol/$H_2O$ (40 ml), collected and air dried to give 4.3 g of product. The two crops were combined, triturated in 80% isopropanol/$H_2O$ (50 ml), collected, air dried and dried in vacuo at 60° to give 6.8 g (0.037 mole, 47% yield), melting point 196°-200° (dec.).

Anal. Calcd. for $C_{11}H_{12}NO_2Na$: C, 61.97; H, 5.67; N, 6.57. Found: C, 62.08; H, 5.88; N, 6.43.

B. N-(2,3-Dihydro-1H-indene-1-yl)-N-(phthaloyl)-glycylglycine

A solution of A. (32.0 g, 0.15 mole) in $H_2O$ (225 ml) was treated simultaneously and dropwise with solutions of NaOH (6.0 g, 0.15 mole) in $H_2O$ (100 ml) and phthaloylglycine acid chloride (34.0 g, 0.15 mole) in THF (210 ml), at 0°-4° over 1.5 hours, using rapid mechanical stirring. Stirring was continued at 0°-4° for one hour and at ambient temperature overnight. Filtered to remove cream-colored, crystalline solid and washed with THF (2×10 ml), ether; melting point 205°-208°, yield: 6.0 g (10.5%). The filtrate was concentrated to ½ volume under the water pump, cooled in an ice bath, and acidified with 20% HCl (15 ml) to pH 4. Then added one volume of ether, stored at R.T. for one hour, collected by filtration the resultant semi-crystalline solid and washed with $H_2O$ (25 ml) and ether. The product was stirred for 15 minutes with isopropanol and the resultant cream-colored, crystalline solid was collected and washed with isopropanol (4×10 ml), ether; melting point 203°-205°, yield: 24.1 g. Combined yield: 6.0+24.1=30.1 g (53%).

An analytical sample was prepared via recrystallization from absolute ethanol, melting point 200°-203°.

Anal. Calcd. for $C_{21}H_{18}N_2O_5$: C, 66.66; H, 4.79; N, 7.40. Found: C, 66.47; H, 4.68; N, 7.31.

C. N-(2,3-Dihydro-1H-indene-1-yl)-N-glycylglycine Hemihydrate

A mixture of B. (20.0 g, 0.053 mole) and $CH_3OH$ (140 ml) was treated dropwise with a solution of 85% $N_2H_4.H_2O$ (3.5 ml, 0.059 mole) in $CH_3OH$ (30 ml) at ambient temperature (24°-26°) over 17 minutes, using mechanical stirring. The reaction solution was heated to 55° over 5 minutes, refluxed for 2.2 hours, and stored at R.T. for 4 hours and in the refrigerator for 4 days. The resultant white, crystalline solid was collected by filtration and washed with $CH_3OH$, yield: 20 g. The solid product mixture was extracted with $H_2O$ (200, 100, and 50 ml) at R.T. and the combined extracts were stripped of solvent under reduced pressure (bath at 35°-52°). The white, crystalline residue was stirred with absolute ethanol (100 ml) at R.T., and the crystalline product was collected by filtration and washed with absolute ethanol (4×20 ml), ether; melting point 176°-178°, yield: 8.9 g (65%).

An analytical sample was prepared by recrystallization from absolute ethanol:$H_2O$ (3:1), melting point 185°-186°.

Anal. Calcd. for $C_{13}H_{16}N_2O_3.H_2O$: C, 60.69; H, 6.66; N, 10.89; $H_2O$, 3.50. Found: C, 61.06; H, 6.57; N, 11.05; $H_2O$, 2.82 2.64.

D. N-(1-Carboxy-3-phenylpropyl)glycyl-N'-(2,3-dihydro 1H-indene-1-yl)glycine Tetartohydrate A mixture of 2-oxo-4-phenylbutanoic acid (7.1 g, 0.040 mole) and $H_2O$ (25 ml) was adjusted to pH 6.68 by the dropwise addition of 50% NaOH. To this solution was added C. (1.8 g, 0.0070 mole) and the mixture was stirred for 10 minutes. A solution of sodium cyanoborohydride (1.4 g, 0.023 mole) and $H_2O$ (25 ml) was added dropwise over 30 minutes. The reaction was stirred for 16 hours to give a solution of pH 8.32. The reaction was diluted with methanol/H$_2$O (3:1) (200 ml), then Dowex 50W-X4 (100–200 mesh) cation exchange resin (200 ml) was added in portions and the mixture was stirred for 2½ hours. The slurry was added to a 62×6 cm column that contained 100 ml of Dowex 50W-X4 resin. The resin was washed with 3 liters of 50% methanol, followed b 2 liters of distilled water. The product was eluted with 2% pyridine (3 liters), and the final 1000 ml of eluent was stripped of solvent in vacuo with the water bath at 12°–18°. The residue was triturated with anhydrous ether (75 ml) and the product was collected by filtration, yield: 1.9 g (65%); melting point 103°–106°.

Anal. Calcd. for $C_{23}H_{26}N_2O_5 \cdot \frac{1}{4}H_2O$: C, 66.57; H, 6.44; N, 6.75; H$_2$O, 1.1. Found: C, 66.34; H, 6.46; N, 6.71; H$_2$O, 4.01 3.48.

What is claimed is:

1. The compound N-(1-carboxy-3-phenylpropyl)glycyl-N'-(2,3-dihydro-1H-indene-1-yl)glycine.

* * * * *

Notice of Adverse Decision in Interference

In Interference No. 101,111, involving Patent No. 4,370,494, G. Wright and R. White, CONVERTING ENZYME INHIBITORS, final judgment adverse to patentees was rendered Feb. 28, 1985, as to claim 1.

[*Official Gazette April 30, 1985.*]